(12) United States Patent
Schiemenz et al.

(10) Patent No.: US 6,645,904 B2
(45) Date of Patent: Nov. 11, 2003

(54) AMINOPHOSPHONIUM COMPOUNDS

(75) Inventors: Berthold Schiemenz, Frankfurt am Main (DE); Thomas Wessel, Frankfurt am Main (DE); Ralf Pfirmann, Griesheim (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/135,252

(22) Filed: Apr. 30, 2002

(65) Prior Publication Data

US 2002/0193592 A1 Dec. 19, 2002

Related U.S. Application Data

(62) Division of application No. 09/617,471, filed on Jul. 17, 2000.

(30) Foreign Application Priority Data

Jul. 23, 1999 (DE) .......................... 199 34 595

(51) Int. Cl.⁷ .................. C07D 265/30; C07D 295/22; C07D 401/02; C07D 401/14; B01J 27/14
(52) U.S. Cl. .................. 502/208; 544/434; 544/424; 544/337; 544/121; 544/84; 546/345; 558/424
(58) Field of Search .................. 546/345; 558/424; 544/434, 84, 121, 337; 502/208

(56) References Cited

U.S. PATENT DOCUMENTS 6,103,659 A   8/2000   Pasenok et al. ............. 502/208

FOREIGN PATENT DOCUMENTS

| WO | WO 98/22413 | 5/1998 |
| WO | WO 98/32532 | 7/1998 |
| WO | WO 99/11588 | 3/1999 |

OTHER PUBLICATIONS

EPO Search Report for application No. 00114362, date Oct. 27, 2000.
Journal of General Chemistry USSR., "Reaction of (1–aziridinyl) phosphonium chlorides with amines", Mar. 20, 1988, p. 2032–2036, XP–002149812.
Derwent Patent Family Abstract for WO 99/11588.
U.S. patent application No. 09/617,470, filed Jul. 17, 2000, Schiemenz, et al.

*Primary Examiner*—Mukund J. Shah
*Assistant Examiner*—Kahsay Habte
(74) *Attorney, Agent, or Firm*—Anthony A. Bisulca

(57) ABSTRACT

The present invention relates to compounds of the formula

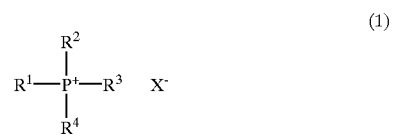

in which one, two or three of the radicals $R^1$, $R^2$, $R^3$ and $R^4$ are

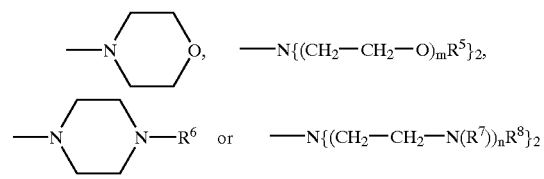

where m and n are an integer from 1 to 10, $R^5$, $R^6$, $R^7$ and $R^8$ are, independently of one another, identical or different and are a straight-chain or branched alkyl radical having 1 to 10 carbon atoms, and the remaining radical(s) $R^1$ to $R^4$ are

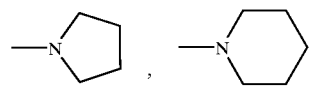

or $-NR^9R^{10}$, where $R^9$ and $R^{10}$ are identical or different and are a straight-chain or branched alkyl radical having 1 to 10 carbon atoms, and $X^-$ is an inorganic or organic anion or an equivalent of a multiply charged inorganic or organic anion. The invention further relates to mixtures of substances comprising compounds of the formula (1), to a process for preparing the compounds of the formula (1) and to the use thereof.

3 Claims, No Drawings

AMINOPHOSPHONIUM COMPOUNDS

CROSS REFERENCE TO RELATED APPLICATION

This application is a divisional application of co-pending U.S. Ser. No. 09/617,471, filed Jul. 17, 2000, the disclosure of which is herein incorporated by reference in its entirety.

BACKGROUND OF THE INVENTION

The present invention relates to novel aminophosphonium compounds, to substance mixtures containing them, and to the preparation and use thereof.

Aminophosphonium compounds are used, as is evident from WO 98/32532 and WO 98/22413, as catalysts for preparing fluorine-containing compounds by a halogen/fluorine exchange reaction (halex reaction). Although the tetrakis(diethylamino)phosphonium bromide used in WO 98/32532 and WO 98/22413 gives good results, it has a very high dermal toxicity which stands in the way of industrial use, however.

SUMMARY OF THE INVENTION

The object is to provide novel compounds which are suitable as catalyst or component of catalyst systems for phase-transfer reactions, in particular for halogen-fluorine exchange reactions, have a lower dermal toxicity and achieve or even exceed the results obtainable on use of tetrakis(diethylamino)phosphonium bromide.

DESCRIPTION OF THE PREFERRED EMBODIMENTS

This object is achieved by compounds of the formula

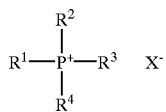

(1)

in which one, two or three of the radicals $R^1$, $R^2$, $R^3$ and $R^4$ are

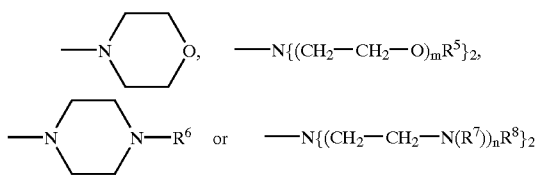

where m and n are an integer from 1 to 10, $R^5$, $R^6$, $R^7$ and $R^8$ are, independently of one another, identical or different and are a straight-chain or branched alkyl radical having 1 to 10 carbon atoms, and the remaining radical(s) $R^1$ to $R^4$ are

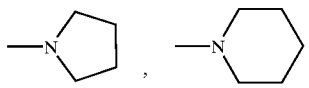

or —$NR^9R^{10}$, where $R^9$ and $R^{10}$ are identical or different and are a straight-chain or branched alkyl radical having 1 to 10 carbon atoms,
and $X^-$ is an inorganic or organic anion or an equivalent of a multiply charged inorganic or organic anion.

Compounds of interest are those of the formula (1) in which one or two of the radicals $R^1$, $R^2$, $R^3$ and $R^4$ are

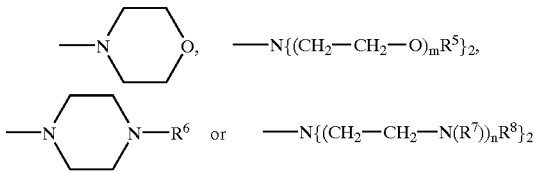

and the remaining radicals $R^1$ to $R^4$ are

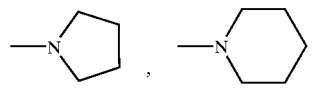

or —$NR^9R^{10}$.

Importance further attaches to compounds of the formula (1) in which m and n are an integer from 1 to 6, and $R^5$, $R^6$, $R^7$, $R^8$, $R^9$ and $R^{10}$ are identical or different and are a straight-chain or branched alkyl radical having 1 to 4 carbon atoms.

The aforementioned radicals $R^1$, $R^2$, $R^3$ and $R^4$ are, in particular,

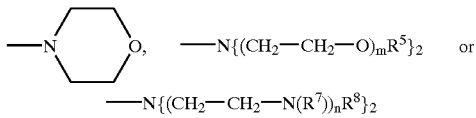

preferably —$N\{(CH_2-CH_2-O)_mR^5\}_2$ or —$N\{(CH_2-CH_2-N(R^7))_nR^8\}_2$, particularly preferably —$N\{(CH_2-CH_2-O)_mR^5\}_2$.

The aforementioned remaining radical(s) $R^1$ to $R^4$ are, in particular,

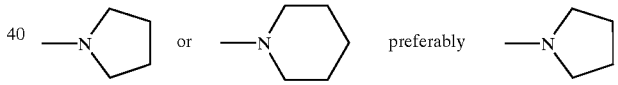

In the compounds of the formula (1), $X^-$ is $F^-$, $Cl^-$, $Br^-$, $I^-$, $ClO_4^-$, $BF_4^-$, $PF_6^-$, $NO_3^-$, $HSO_4^-$, ½ $SO_4^{2-}$, $H_2PO_4^-$, ½ $HPO_4^{2-}$, ⅓ $PO_4^{3-}$, R'—$COO^-$, where R' is an alkyl radical having 1 to 9 carbon atoms, a phenyl radical, benzyl radical or naphthyl radical, R"—$SO_3$, where R" is an alkyl radical having 1 to 18 carbon atoms, a phenyl radical, tolyl radical or naphthyl radical, $HCO_3^-$, ½ $CO_3^{2-}$ or ½ $C_6H_4(COO^-)_2$.

$X^-$ is, in particular, $F^-$, $Cl^-$, $Br^-$, $I^-$, $BF_4^-$, $PF_6^-$ or ½ $SO_4^{2-}$, preferably $F^-$, $Cl^-$, or $Br^-$, particularly preferably $Cl^-$.

The following aminophosphonium compounds (aminophosphonium salts) may be mentioned as examples without claiming completeness.

Bis(2-methoxyethyl)amino-tris(pyrrolidino)phosphonium chloride

Di(bis(2-methoxyethyl)amino)-bis(pyrrolidino) phosphonium chloride

Tri(bis(2-methoxyethyl)amino)-(pyrrolidino)phosphonium chloride

Bis(methyl-diethoxyethylene)amino-tris(pyrrolidino) phosphonium chloride

Di(bis(methyl-diethoxyethylene)amino)-bis(pyrrolidino) phosphonium chloride

Tri(bis(methyl-diethoxyethylene)amino)-(pyrrolidino) phosphonium chloride

Bis(methyl-tetraethoxyethylene)amino-tris(pyrrolidino) phosphonium chloride
Di(bis(methyl-tetraethoxyethylene)amino-bis(pyrrolidino) phosphonium chloride
Tri(bis(methyl-tetraethoxyethylene)amino)-(pyrrolidino) phosphonium chloride
Morpholino-tris(pyrrolidino)phosphonium chloride
Dimorpholino-bis(pyrrolidino)phosphonium chloride
Trimorpholino-(pyrrolidino)phosphonium chloride
Bis(2-methoxyethyl)amino-tris(piperidino)phosphonium chloride
Di(bis(2-methoxyethyl)amino)-bis(piperidino) phosphonium chloride
Tri(bis(2-methoxyethyl)amino)-(piperidino)phosphonium chloride
Bis(methyl-diethoxyethylene)amino-tris(piperidino) phosphonium chloride
Di(bis(methyl-diethoxyethylene)amino)-bis(piperidino) phosphonium chloride
Tri(bis(methyl-diethoxyethylene)amino)-(piperidino) phosphonium chloride
Bis(methyl-tetraethoxyethylene)amino-tris(piperidino) phosphonium chloride
Di(bis(methyl-tetraethoxyethylene)amino)-bis(piperidino) phosphonium chloride
Tri(bis(methyl-tetraethoxyethylene)amino)-(piperidino) phosphonium chloride
Morpholino-tris(piperidino)phosphonium chloride
Dimorpholino-bis(piperidino)phosphonium chloride
Bis(2-methoxyethyl)amino-tris(diethylamino)phosphonium chloride
Di(bis(2-methoxyethyl)amino)-bis(diethylamino) phosphonium chloride
Tri(bis(2-methoxyethyl)amino)-(diethylamino) phosphonium chloride
Bis(methyl-tetraethoxyethylene)amino-tris(diethylamino) phosphonium chloride
Di(bis(methyl-tetraethoxyethylene)amino-bis (diethylamino)phosphonium chloride
Tri(bis(methyl-tetraethoxyethylene)amino)-(diethylamino) phosphonium chloride
Morpholino-tris(diethylamino)phosphonium chloride
Dimorpholino-bis(diethylamino)phosphonium chloride
Trimorpholino-(diethylamino)phosphonium chloride
Bis(2-methoxyethyl)amino-tris(dimethylamino) phosphonium chloride
Di(bis(2-methoxyethyl)amino)-bis(dimethylamino) phosphonium chloride
Tri(bis(2-methoxyethyl)amino)-(dimethylamino) phosphonium chloride
Bis(methyl-bisethoxyethylene)amino-tris(dimethylamino) phosphonium chloride
Di(bis(methyl-bisethoxyethylene)amino)-bis (dimethylamino)phosphonium chloride
Tri(bis(methyl-bisethoxyethylene)amino)-(dimethylamino) phosphonium chloride
Bis(methyl-tetraethoxyethylene)amino-tris(dimethylamino) phosphonium chloride
Di(bis(methyl-tetraethoxyethylene)amino)-bis (dimethylamino)phosphonium chloride
Tri(bis(methyl-tetraethoxyethylene)amino)-(dimethylamino)phosphonium chloride
Tris(dimethylamino)-morpholino-phosphonium chloride
Bis(dimethylamino)-dimorpholino-phosphonium chloride
Dimethylamino-trimorpholino-phosphonium chloride
Bis(2-methoxyethyl)amino-tris(butyl-ethylamino) phosphonium chloride
Di(bis(2-methoxyethyl)amino)-bis(butyl-ethylamino) phosphonium chloride
Tri(bis(2-methoxyethyl)amino)-(butyl-ethylamino) phosphonium chloride
Bis(methyl-tetraethoxyethylene)amino-tris(butyl-ethylamino)phosphonium chloride
Di(bis(methyl-tetraethoxyethylene)amino)-bis(butyl-ethylamino)phosphonium chloride
Tri(bis(methyl-tetraethoxyethylene)amino)-(butyl-ethylamino)phosphonium chloride
Tris(butyl-ethylamino)-morpholino-phosphonium chloride
Bis(butyl-ethylamino)-dimorpholino-phosphonium chloride
(Butyl-ethylamino)-trimorpholino-phosphonium chloride
N-Methylpiperazino-tris(pyrrolidino)phosphonium chloride
Bis(N-methylpiperazino)-bis(pyrrolidino)phosphonium chloride
Tris(N-methylpiperazino)-(pyrrolidino)phosphonium chloride
N-Methylpiperazino-tris(diethylamino)phosphonium chloride
Bis(N-methylpiperazino)-bis(diethylamino)phosphonium chloride
Tris(N-methylpiperazino)-(diethylamino)phosphonium chloride
N-Methylpiperazino-tris(dimethylamino)phosphonium chloride
Bis(N-methylpiperazino)-bis(dimethylamino)phosphonium chloride
Tris(N-methylpiperazino)-(dimethylamino)phosphonium chloride
N-Methylpiperazino-tris(butyl-ethylamino)phosphonium chloride
Bis(N-methylpiperazino)-bis(butyl-ethylamino) phosphonium chloride
Tris(N-methylpiperazino)-(butyl-ethylamino)phosphonium chloride In place of the listed aminophosphonium chlorides it is also possible to employ, for example, the corresponding bromides, iodides, fluorides, sulfates, hydrogen sulfates, acetates or phthalates.

The present invention also relates to mixtures of substances comprising at least one compound of the formula

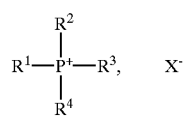

(1)

in which $R^1, R^2, R^3, R^4$ and $X^-$ have the above meaning, and at least one compound selected from the group of quaternary ammonium compounds of the formula

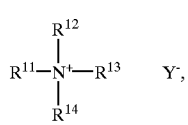

(2)

quaternary ammonium salts or phosphonium salts of the formula

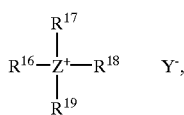
(3)

polyethers of the formula $R^{20}$—$(O$—$C_xH_{2x})_s$—$OR^{21}$ (4) and crown ethers,
in which in formula (2) $R^{11}$, $R^{12}$ and $R^{13}$ are identical or different and are a linear or branched radical of the formula —$(C_pH_{2p}O)_rR^{15}$ in which $R^{15}$ is hydrogen or a linear or branched alkyl radical having 1 to 16 carbon atoms, p is an integer from 1 to 10 and r is an integer from 1 to 15;
or a linear or branched alkyl radical having 1 to 30 carbon atoms;
or an unsubstituted phenyl or naphthyl radical, or a substituted phenyl or naphthyl radical, where the substituents have the meaning of halogen, $C_1$–$C_4$-alkyl, $C_1$–$C_4$-alkoxy, nitro or cyano;
$R^{14}$ is a linear or branched radical of the formula —$(C_pH_{2p}O)_rR^{15}$ and
$Y^-$ is an inorganic anion;
and in formula (3)
$R^{16}$, $R^{17}$, $R^{18}$ and $R^{19}$ are identical or different and are a linear or branched alkyl radical having 1 to 22 carbon atoms; or an unsubstituted or substituted aryl radical or a $C_1$–$C_4$-alkylaryl radical, where aryl has the meaning of phenyl or naphthyl, and said substituents are halogen, $C_1$–$C_4$-alkyl, $C_1$–$C_4$-alkoxy, nitro or cyano; Z has the meaning of N or P, and $Y^-$ is an inorganic anion;
and in formula (4)
$R^{20}$ and $R^{21}$ are identical or different and are a linear or branched alkyl radical having 1 to 16 carbon atoms;
x is an integer from 2 to 6 and
s is an integer from 1 to 60;
or one of the radicals $R^{20}$ and $R^{21}$ is hydrogen and the other one of the radicals is a linear or branched alkyl radical having 1 to 16 carbon atoms,
x is an integer from 2 to 6 and s is an integer from 2 to 50,
or the radicals $R^{20}$ and $R^{21}$ are hydrogen, x is an integer from 2 to 6 and s is an integer from 3 to 5.

The present invention relates in particular to mixtures of substances which comprise at least one compound of the formula (1) and at least one compound selected from the group of quaternary ammonium compounds of the formula (2), quaternary ammonium salts and phosphonium salts of the formula (3), polyethers of the formula (4) and crown ethers, in which in formula (2) $R^{11}$, $R^{12}$ and $R^{13}$ are identical or different and are a linear or branched radical of the formula —$(C_pH_{2p}O)_rR^{15}$ in which $R^{15}$ is hydrogen or a linear or branched alkyl radical having 1 to 8 carbon atoms, p is an integer from 1 to 5 and r is an integer from 2 to 10; or a linear or branched alkyl radical having 1 to 18 carbon atoms; or an unsubstituted phenyl or naphthyl radical; $R^{14}$ is a linear or branched radical of the formula —$(C_pH_{2p}O)_rR^{15}$, in which $R^{15}$ is hydrogen or a linear or branched alkyl radical having 1 to 8 carbon atoms, p is an integer from 1 to 5 and r is an integer from 2 to 10; and $X^-$ is fluoride, chloride, bromide, $SO_4^{2-}/2$ or hydrogen sulfate.

Mixtures of substances of particular interest are those comprising at least one compound of the formula (1) and at least one compound from the group of quaternary ammonium compounds of the formula (2).

Mention should also be made of mixtures of substances of the above type comprising at least one ammonium salt or phosphonium salt of the formula (3), in which in formula (3) $R^{16}$, $R^{17}$, $R^{18}$ and $R^{19}$ are identical or different and are a linear or branched alkyl radical having 1 to 16 carbon atoms; or an unsubstituted or substituted aryl radical or a $C_1$–$C_4$-alkylaryl radical, where aryl has the meaning of phenyl or naphthyl, and said substituents are halogen, $C_1$–$C_4$-alkyl, $C_1$–$C_4$-alkoxy, nitro or cyano.

Mixtures of substances of the above type comprising at least one polyether of the formula (4) or crown ether, in which in formula (4) $R^{20}$ and $R^{21}$ are identical or different and are hydrogen or a linear or branched alkyl radical having 1 to 8 carbon atoms, x is an integer from 2 to 3 and s is an integer from 4 to 50, are likewise of interest.

The mixtures of substances normally comprise from 5 to 95% by weight, in particular 20 to 80% by weight, preferably 25 to 75% by weight, of at least one compound of the formula (1). The residual 95 to 5% by weight, in particular 80 to 20% by weight, preferably 75 to 25% by weight, of the mixtures of substances account for the remainder, namely at least one compound selected from the group of quaternary ammonium compounds of the formula (2) of quaternary ammonium or phosphonium salts of the formula (3), polyethers of the formula (4) and crown ethers, in particular at least one compound from the group of quaternary ammonium compounds of the formula (2).

The present invention further relates to a process for preparing compounds of the formula

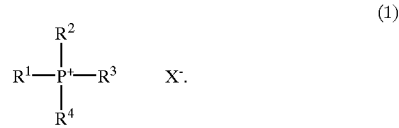
(1)

It comprises reacting a phosphorus pentahalide in the presence of an inert solvent at −70 to 140° C., in particular −30 to 120° C., preferably −15 to 60° C., with from 1 to 6 mol, in particular 1 to 2.5 mol, of

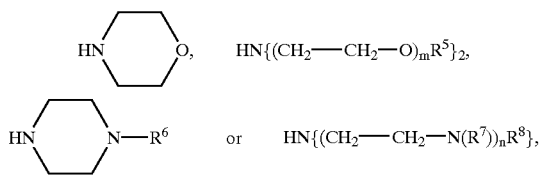

per halogen equivalent to be exchanged, and subsequently reacting the reaction product with from 1 to 10 mol, in particular 1 to 3 mol, of

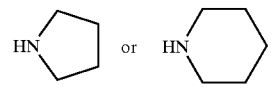

or $HNR^9R^{10}$ per halogen equivalent still to be exchanged. This reaction of the reaction product takes place at −15 to 140° C., in particular 0 to 130° C., preferably 20 to 130° C.

The phosphorus pentahalide employed is $PCl_5$ or $PBr_5$, in particular $PCl_5$.

The inert solvent employed is an aliphatic, cycloaliphatic or aromatic hydrocarbon or a mono- or polychlorinated aliphatic, cycloaliphatic or aromatic hydrocarbon.

Very suitable inert solvents are, for example, hexane, cyclohexane, methylcyclohexane, toluene, ethylbenzene, mesitylene, o-xylene, m-xylene, p-xylene, technical mixtures of isomeric xylenes, methylene chloride, tetrachloroethane, chlorobenzene, dichlorobenzene or chlorotoluene. It is also possible to use mixtures of solvents.

The phosphorus pentahalide is suspended or dissolved in the inert solvent and the reaction is carried out with the addition of the aforementioned nitrogen-containing compounds.

This results in compounds of the formula (1) in which X$^-$ is a halide. If required, the halide can be exchanged for another one of the aforementioned anions by metathesis.

The invention further relates to the use of the compounds of the formula (1) as catalyst and cocatalyst for phase-transfer reactions, nucleophilic substitutions and halogen-fluorine exchange reactions.

The invention further relates to the use of the mixtures of substances comprising at least one compound of the formula (1) and at least one compound selected from the group of quaternary ammonium compounds of the formula (2), quaternary ammonium salts or phosphonium salts of the formula (3), polyethers of the formula (4) and crown ethers as catalyst for phase-transfer reactions, nucleophilic substitutions and halogen-fluorine exchange reactions.

EXAMPLES

The following examples describe the present invention further without restricting it.
Experimental Section
Preparation of the Aminophosphonium Compounds (Aminophosphonium Salts)

Example 1

Bis(2-methoxyethyl)amino-tris(pyrrolidino) phosphonium Chloride 104.12 g (0.5 mol) of phosphorus pentachloride are introduced into 400 g of chlorobenzene and cooled to −20 to −10° C. At this temperature, 66.89 g (0.5 mol) of bis-(2-methoxyethyl)amine are added dropwise in such a way that the internal temperature does not exceed 0° C. After the addition, the mixture is allowed to warm slowly to 30° C. and is then heated at 90–100° C. for one hour.

It is then cooled again to 10° C., and 214.5 g (3.0 mol) of pyrrolidine are added dropwise in such a way that the internal temperature does not exceed 15° C. After the addition, the mixture is heated to reflux for two hours.

After cooling to 0° C., 779.94 g (3.9 mol) of 20% strength sodium hydroxide solution are cautiously used to make alkaline. The aqueous phase is separated off and discarded. Excess amine is then distilled out of the organic phase. After the end of the distillation, HCl is used to acidify to pH=6–7 and, after filtration, the chlorobenzene is stripped off in a rotary evaporator.

Elemental analysis: C=55.2%, H=8.9%, N=12.9%, P=7.0%, Cl=8.2%

Example 2

Bis(bis(2-methoxyethyl)amino)-bis(pyrrolidino) phosphonium Bromide 104, 12 g (0.5 mol) of phosphorus pentachloride are introduced into 400 g of chlorobenzene and cooled to −20 to 10° C. At this temperature, 133.78 g (1 mol) of bis-(2-methoxyethyl)amine are added dropwise in such a way that the internal temperature does not exceed 0° C. After the addition, the mixture is heated at 100° C. for one hour.

It is then cooled again to 10° C., and 214.55 g (3.0 mol) of pyrrolidine are added dropwise in such a way that the internal temperature does not exceed 15° C. After the addition, the mixture is heated to reflux for two hours. After cooling to 0° C., 779.94 g (3.9 mol) of 20% strength sodium hydroxide solution (equivalent to 155.99 g of NaOH) are cautiously used to make alkaline. The aqueous phase is separated off and discarded. After addition of 71.93 g (0.6 mol) of potassium bromide, excess free amine is distilled out of the organic phase. After the end of the distillation, HBr is used to acidify to pH=6–7 and, after filtration, the chlorobenzene is stripped off in a rotary evaporator.

Elemental analysis: C=46.9%, H=8.8%, N=10.6%, P=5.9%, Br=15.2%, Cl=0.14%

Example 3

(n-Butyl-ethylamino)-tris-(pyrrolidino)phosphonium Bromide 42.7 g (0.6 mol) of pyrrolidine are added dropwise to 20.8 g (0.1 mol) of PCl$_5$ in 100 ml of chlorobenzene in 1 hour so that the internal temperature does not exceed 15° C. After the addition, the mixture is stirred at 50° C. for one hour and then, at a reaction temperature of 25° C., 16 g (0.22 mol) of n-butylamine are added.

After 1 hour under reflux, the mixture is again cooled to 25° C. and hydrolyzed with 200 ml of ice-water, and the aqueous phase is separated off. After the excess amine has been distilled off, 19.9 g (0.5 mol) of NaOH in 20 ml of water are introduced. At 50° C., 12.0 g (0.11 mol) of ethyl bromide are added dropwise. After stirring at 70° C. for 3 hours, the mixture is cooled to 25° C. and diluted with 200 ml of water. The organic phase is separated off and acidified to pH=6–7 with 60% strength hydrobromic acid. After all the volatile constituents have been distilled off, 33.6 g (n-butyl-ethylamino)-tris-(pyrrolidino)phosphonium bromide are obtained as a pale brownish oil.

Example 4

Bis(methyl-tetraethoxyethylene)amino-tris (pyrrolidino)phosphonium Chloride

Bis(methyl-tetraethoxyethylene)amino-tris(pyrrolidino) phosphonium chloride is prepared in analogy to Example 1 from 104.12 g (0.5 mol) of phosphorus pentachloride, 198.75 g (0.5 mol) of bis-(methyl-tetraethoxyethylene) amine (=HN{(CH$_2$—CH$_2$—O)$_4$CH$_3$}$_2$) and 214.55 g (3.0 mol) of pyrrolidine.

Elemental analysis: C=53.6%, H=9.6%, N=8.1%, P=4.3%, Cl=5.6%

Example 5

Bis(bis(methyl-tetraethoxyethylene)amino)-bis (pyrrolidino)phosphonium Chloride

Bis(bis(methyl-tetraethoxyethylene)amino)-bis (pyrrolidino)phosphonium chloride is prepared in analogy to Example 2 from 104.12 g (0.5 mol) of phosphorus pentachloride, 397.51 g (1 mol) of bis-(methyl-tetraethoxyethylene)amine (=HN{(CH$_2$—CH$_2$—O)$_4$CH$_3$}$_2$) and 214.55 g (3.0 mol) of pyrrolidine.

Elemental analysis: C=44.7%, H=8.3%, N=6.5%, P=3.7%, Cl=4.5%

Example 6

Tris(2-methoxyethyl)amino-(diethylamino) phosphonium Bromide 104.12 g (0.5 mol) of phosphorus pentachloride are introduced into 400 g of chlorobenzene and cooled to −20 to −10° C. At a reaction temperature of <5° C., 401.34 g (3 mol) of bis-(2-methoxyethyl)amine are added dropwise. After the addition, the mixture is slowly allowed to warm to 30° C. and is then heated at 100° C. for one hour.

At 20° C., 36 g (2.1 mol) of ammonia are passed in. After hydrolysis with 850 g of 20% strength aqueous sodium hydroxide solution, the chlorobenzene and the excess bis(2-methoxyethyl)amine are distilled out of the organic phase (120° C., 10 mbar). The oily residue is taken up in 300 ml of chlorobenzene, and 340 g of 50% strength aqueous sodium hydroxide solution are added. At 50° C., 119 g (1.1 mol) of ethyl bromide are added dropwise, and the mixture is then stirred at 70° C. for three hours to complete the reaction. Then, at 20° C., 350 ml of water are added and, after phase separation, the organic phase is neutralized with 24 g of 36% strength hydrobromic acid. Removal of all volatile constituents by distillation results in 33.6 g of tris(2-methoxyethyl)amino-(diethylamino)phosphonium bromide as a brownish oil.

Elemental analysis: C=36.1%, H=7.9%, N=7.5%, P=4.15%, Br=9.8%, Cl=0.5%.

Example 7

N-Methylpiperazino-tris(pyrrolidino)phosphonium Chloride 41.65 g (0.2 mol) of phosphorus pentachloride are introduced into 200 g of toluene and cooled to −20° C. Then 20.03 g (0.2 mol) of N-methylpiperazine are added dropwise in such a way that the internal temperature does not exceed 5° C. After the addition, the mixture is heated at 100° C. for one hour.

At 10° C., 56.9 g (0.8 mol) of pyrrolidine are added dropwise. After the addition, the mixture is allowed to warm slowly to 20° C. After a further 30 min, it is heated to reflux for two hours.

After hydrolysis with 20% strength aqueous sodium hydroxide solution, the toluene and the excess amine are distilled out of the organic phase (120° C., 10 mbar). 69.6 g of N-methylpiperazino-tris(pyrrolidino)phosphonium chloride are obtained as a brownish oil.

Elemental analysis: C=54.3%, H=9.6%, N=18.5%, P=8.15%, Cl=9.7%

Example 8

Dioctylamino-tris(pyrrolidino)phosphonium Chloride

Dioctylamino-tris(pyrrolidino)phosphonium chloride is prepared in analogy to Example 1 from 41.65 g (0.2 mol) of phosphorus pentachloride, 48.3 g (0.2 mol) of dioctylamine and 99.6 g (1.4 mol) of pyrrolidine.

Elemental analysis: C=65.3%, H=11.6%, N=10.5%, P=5.9%, Cl=7.0%

Example 9

Morpholino-tris(pyrrolidino)phosphonium Chloride

Morpholino-tris(pyrrolidino)phosphonium chloride is prepared in analogy to Example 1 from 104.12 g (0.5 mol) of phosphorus pentachloride, 43.6 g (0.5 mol) of morpholine and 214.6 g (3.0 mol) of pyrrolidine.

Elemental analysis: C=52.8%, H=9.0%, N=15.3%, P=8.4%, Cl=10.1%

The corresponding bromide is obtained by salts metathesis in analogy to Example 2.

Example 10

Bis(morpholino)-bis(pyrrolidino)phosphonium Chloride

Bis(morpholino)-bis(pyrrolidino)phosphonium chloride is prepared in analogy to Example 2 from 104.12 g (0.5 mol) of phosphorus pentachloride, 87.12 g (1 mol) of morpholine and 214.55 g (3.0 mol) of pyrrolidine.

Elemental analysis: C=50.6%, H=8.7%, N=14.6%, P=8.0%, Cl=9.5%

The corresponding bromide is obtained by salt metathesis in analogy to Example 2.

Example 11

Bis(2-methoxyethyl)amino-tris(piperidino) phosphonium Chloride

Bis(2-methoxyethyl)amino-tris(piperidino)phosphonium chloride is prepared in analogy to Example 2 from 104.12 g (0.5 mol) of phosphorus pentachloride, 66.9 g (0.5 mol) of bis-(2-methoxyethyl)amine and 255.4 g (3.0 mol) of piperidine.

Example 12

Bis(bis(2-methoxyethyl)amino)-bis(piperidino) phosphonium Chloride

Bis(bis(2-methoxyethyl)amino)-bis(piperidino) phosphonium chloride is prepared in analogy to Example 1 from 104.12 g (0.5 mol) of phosphorus pentachloride, 133.2 g (1 mol) of bis-(2-methoxyethyl)amine and 212.9 g (2.5 mol) of piperidine.

Comparative Example A

Tetrakis(diethylamino)phosphonium Bromide (Comparison Substance)

109.7 g (1.5 mol) of diethylamine are added dropwise to a 52.1 g (0.25 mol) of PCl$_5$ in 220 ml of chlorobenzene in 1 hour so that the internal temperature does not exceed 5° C. After the addition, the mixture is stirred at 30° C. for one hour and then, at T=15° C., 30 g of ammonia are passed in.

After 1 hour, 340 g of 20% strength sodium hydroxide solution are added, and the aqueous phase is separated off. The excess diethylamine is distilled out of the organic phase. Then 170 g of 50% strength sodium hydroxide solution and 60 g (0.55 mol) of ethyl bromide are added, and the mixture is heated at 50° C. for 4 hours. After phase separation, the organic phase is acidified to pH=6–7 with 60% strength hydrobromic acid. Removal of all the volatile constituents by distillation results in 83.9 g of tetrakis(diethylamino) phosphonium bromide as a pale brownish oil.

Comparative Example B

Tris(dibutylamino)-(diethylamino)phosphonium Bromide (Comparison Substance)

Tris(dibutylamino)-(diethylamino)phosphonium bromide is prepared in analogy to Comparative Example A from 41.65 g (0.2 mol) of phosphorus pentachloride, 77.50 g (0.6 mol) of dibutylamine, an excess of ammonia and 47.9 g (0.44 mol) of ethyl bromide.

Elemental analysis: C=53.2%, H=10.9%, N=12.3%, P=6.75%, Br=16.3%, Cl=0.7%

Testing of the Catalytic Activity:

Preparation of 2,6-difluorobenzaldehyde (DFBAL) from 2-chloro-6-fluorobenzaldehyde (CFBAL) by chlorine-fluorine exchange reaction

Comparative Example 1A and 1B

At 60° C., 4.4 g (0.01 mol) of tetrakis(diethylamino)phosphonium bromide (Comparative Example 1 A) or 5.7 g (0.01 mol) of tris(dibutylamino)-(diethylamino)phosphonium bromide (Comparative Example 1 B) and, in each case, 17.6 g (0.03 mol) of methyl-tris(methyltetraethoxy)ammonium chloride [{CH$_3$—(O—C$_2$H$_4$)$_4$}$_3$NCH$_3$]Cl, 58.3 g (1 mol) of potassium fluoride and 10 ml of chlorobenzene are successively added to 158.6 g (1 mol) of 2-chloro-6-fluorobenzaldehyde (CFBAL). The reaction mixture is dried by azeotropic distillation of the chlorobenzene under reduced pressure. After 20 hours at 170° C., the formation of 2,6-difluorobenzaldehyde (DFBAL) and the conversion in the reaction are determined by gas chromatography.

EXAMPLES

In the following examples identified by an * in Table 1, in place of tetrakis(diethylamino)phosphonium bromide there is used an equivalent molar quantity of the aminophosphonium salt indicated in each case in Table 1 (0.01 mol in each case) and 0.03 mol of methyl-tris(methyltetraethoxy)ammonium chloride. The procedure is otherwise analogous to Comparative Example 1A.

The numerical data in Table 1 correspond to GC percentage areas. The difference from 100% (remainder) which is likewise indicated in Table 1 is a measure of side reactions and decomposition.

TABLE 1

Yield of 2,6-difluorobenzaldehyde (DFBAL) from the halex reaction of 2-chloro-6-fluorobenzaldehyde (CFBAL) in GC % areas

| Aminophosphonium salt | DFBAL | CFBAL | Remainder |
|---|---|---|---|
| No catalysts | 16.2 | 72.1 | 11.7 |
| [(Et$_2$N)$_4$P]Br | 56.1 | 24.7 | 19.2 |
| [(Bu$_2$N)$_3$(Et$_2$N)P]Br | 63.0 | 20.1 | 16.9 |
| [(Me(OCH$_2$CH$_2$)$_2$N)(pyrrolidino)$_3$P]Br * | 68.9 | 15.0 | 16.1 |
| [(Me(OCH$_2$CH$_2$)$_2$N)(pyrrolidino)$_3$P]Cl * | 67.7 | 17.8 | 14.5 |
| [(Me(OCH$_2$CH$_2$)$_2$N)$_2$(pyrrolidino)$_2$P]Br * | 70.2 | 12.3 | 17.5 |
| [{(Et)(Bu)N}(pyrrolidino)$_3$P Br * | 64.4 | 22.6 | 13.0 |
| [{(Me(O—C$_2$H$_4$)$_4$)$_2$N}(pyrrolidino)$_3$P]Br * | 71.5 | 18.4 | 10.1 |
| [{(Me(O—C$_2$H$_4$)$_4$)$_2$N}$_2$(pyrrolidino)$_2$P]Br * | 70.8 | 17.2 | 12.0 |
| [(N-Me(piperazino)(pyrrolidino)$_3$P]Cl * | 68.2 | 18.2 | 13.6 |
| [(Morpholino)(pyrrolidino)$_3$P]Br * | 68.5 | 18.1 | 13.4 |
| [(Morpholino)(pyrrolidino)$_3$P]Cl * | 68.2 | 17.1 | 14.7 |
| [(Morpholino)$_2$(pyrrolidino)$_2$P]Br * | 66.3 | 19.7 | 14.0 |
| [(Morpholino)$_2$(pyrrolidino)$_2$P]Cl * | 65.8 | 20.1 | 14.1 |
| [(Me(OCH$_2$CH$_2$)$_2$N)(piperidino)$_3$]Cl * | 71.2 | 16.8 | 12.0 |
| [(Me(OCH$_2$CH$_2$)$_2$N)$_2$(piperidino)$_2$P]Cl * | 70.4 | 18.2 | 11.4 |

* Examples

Testing of the Catalytic Activity:

Preparation of 2,6-difluorobenzaldehyde (DFBAL) and 2-chloro-6-fluorobenzaldehyde (CFBAL) from 2,6-dichlorobenzaldehyde (DCBAL) by chlorine-fluorine exchange reaction.

Comparative Example 2A and 2B

At 60° C., 8.8 g (0.02 mol) of tetrakis(diethylamino)phosphonium bromide (Comparative Example 2 A) or 11.35 g (0.02 mol) of tris(dibutylamino)(diethylamino)phosphonium bromide (Comparison Example 2 B) and, in each case, 35.2 g (0.06 mol) of methyl-tris(methyltetraethoxy)ammonium chloride, 116.2 g (2 mol) of potassium fluoride and 10 ml of chlorobenzene are successfully added to 175.0 g (1 mol) of 2,6-dichlorobenzaldehyde (DCBAL). The reaction mixture is dried by azeotropic distillation of the chlorobenzene under reduced pressure. After 20 hours at 165° C., the formation of 2-chloro-6-fluorobenzaldehyde (CFBAL) and 2,6-difluorobenzaldehyde (DFBAL) and the conversion in the reaction are determined by gas chromatography.

EXAMPLES

In the following examples identified by an * in Table 2, in place of tetrakis-(diethylamino)phosphonium bromide there is used an equivalent molar quantity of the aminophosphonium salt indicated in each case (0.02 mol in each case) and 0.06 mol of methyl-tris(methyltetraethoxy)ammonium chloride. The procedure is otherwise analogous to Comparative Example 2A.

The numerical data in Table 2 correspond to GC percentage areas. The difference from 100% (remainder) which is likewise indicated in Table 2 is a measure of side reactions and decomposition.

TABLE 2

Yields of 2,6-difluorobenzaldehyde (DFBAL) and 2-chloro-6-fluorobenzaldehyde (CFBAL) from the halex reaction of 2,6-dichlorobenzaldehyde (DCBAL) in GC % areas

| Aminophosphonium salt | DFBAL | CFBAL | DCBAL | Remainder |
|---|---|---|---|---|
| no catalyst | 1.2 | 11.4 | 71.5 | 15.9 |
| [(Et$_2$N)$_4$P]Br | 40.2 | 26.9 | 11.2 | 21.7 |
| [(Bu$_2$N)$_3$(Et$_2$N)P]Br | 41.1 | 27.5 | 10.4 | 21.0 |
| [(Me(OCH$_2$CH$_2$)$_2$N)(pyrrolidino)$_3$P]Br * | 51.1 | 36.1 | 1.8 | 11.0 |
| [(Me(OCH$_2$CH$_2$)$_2$N)(pyrrolidino)$_3$P]Cl * | 50.7 | 37.8 | 2.1 | 9.4 |
| [(Me(OCH$_2$CH$_2$)$_2$N)$_2$(pyrrolidino)$_2$P]Br * | 50.6 | 37.3 | 1.4 | 10.7 |
| [{(Et)(Bu)N}(pyrrolidino)$_3$P] Br * | 43.6 | 31.2 | 8.6 | 16.6 |
| [(Octyl$_2$N)(pyrrolidino)$_3$P]Br * | 41.6 | 33.5 | 8.1 | 16.8 |

TABLE 2-continued

Yields of 2,6-difluorobenzaldehyde (DFBAL) and 2-chloro-6-fluorobenzaldehyde (CFBAL) from the halex reaction of 2,6-dichlorobenzaldehyde (DCBAL) in GC % areas

| Aminophosphonium salt | DFBAL | CFBAL | DCBAL | Remainder |
|---|---|---|---|---|
| [{(Me(O—C$_2$H$_4$)$_4$)$_2$N}(pyrrolidino)$_3$P]Br * | 53.8 | 31.4 | 3.9 | 10.9 |
| [{(Me(O—C$_2$H$_4$)$_4$)$_2$N}$_2$(pyrrolidino)$_2$P]Br * | 50.4 | 36.8 | 2.1 | 10.7 |
| [(N-Me(piperazino)(pyrrolidino)$_3$P]Cl * | 46.9 | 38.2 | 4.4 | 10.5 |
| [(Morpholino)(pyrrolidino)$_3$P]Br * | 46.9 | 32.3 | 5.1 | 15.7 |
| [(Morpholino)(pyrrolidino)$_3$P]Cl * | 47.2 | 34.8 | 5.4 | 12.6 |
| [(Morpholino)$_2$(pyrrolidino)$_2$P]Br * | 47.8 | 35.6 | 5.2 | 11.4 |
| [(Morpholino)$_2$(pyrrolidino)$_2$P]Cl * | 49.6 | 31.9 | 4.8 | 13.7 |
| [(Me(OCH$_2$CH$_2$)$_2$N)(piperidino)$_3$P]Cl * | 54.2 | 34.4 | 1.7 | 9.7 |
| [(Me(OCH$_2$CH$_2$)$_2$N)$_2$(piperidino)$_2$P]Cl * | 53.1 | 35.5 | 1.5 | 9.9 |

* Examples

In Tables 1 and 2, Me stands for methyl, Et for ethyl and Bu for butyl, Me(O—C$_2$H$_4$)$_4$ for methyltetraethoxyethylene Pyrrolidino for

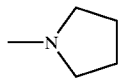

Morpholino for

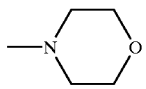

N-Me(piperazino) for

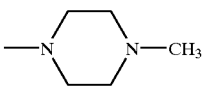

and piperidino for

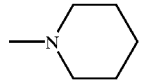

What is claimed is:

1. A mixture of substances comprising at least one compound of the formula

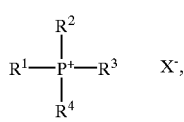

in which one, two or three of the radicals $R^1$, $R^2$, $R^3$ and $R^4$ are

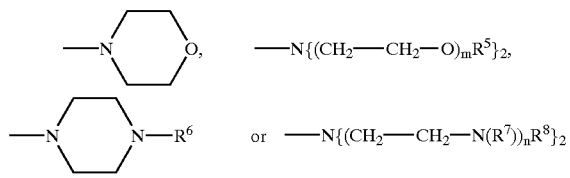

where m and n are an integer from 1 to 10, $R^5$, $R^6$, $R^7$ and $R^8$ are, independently of one another, identical or different and are a straight-chain or branched alkyl radical having 1 to 10 carbon atoms, and the remaining radical(s) $R^1$ to $R^4$ are

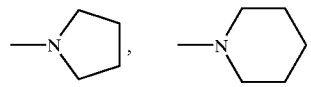

$X^-$ is an inorganic or organic anion or an equivalent of a multiply charged inorganic or organic anion
and at least one compound selected from the group of quaternary ammonium compounds of the formula

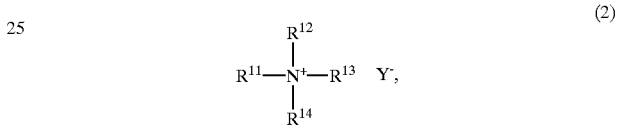

quaternary ammonium salts or phosphonium salts of the formula

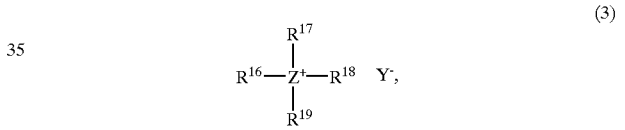

polyethers of the formula $R^{20}$—(O—C$_x$H$_{2x}$)$_s$—OR$^{21}$ (4) and crown ethers,
in which in formula (2) $R^{11}$, $R^{12}$ and $R^{13}$ are identical or different and are a linear or branched radical of the formula —(C$_p$H$_{2p}$O)$_r$R$^{15}$ in which $R^{15}$ is hydrogen or a linear or branched alkyl radical having 1 to 16 carbon atoms, p is an integer from 1 to 10 and r is an integer from 1 to 15; or a linear or branched alkyl radical having 1 to 30 carbon atoms; or an unsubstituted phenyl or naphthyl radical, or a substituted phenyl or naphthyl radical, where the substituents have the meaning of halogen, C$_1$–C$_4$-alkyl, C$_1$–C$_4$-alkoxy, nitro or cyano; $R^{14}$ is a linear or branched radical of the formula —(C$_p$H$_{2p}$O)$_r$R$^{15}$ and $Y^-$ is an inorganic anion; and in formula (3) $R^{16}$, $R^{17}$, $R^{18}$ and $R^{19}$ are identical or different and are a linear or branched alkyl radical having 1 to 22 carbon atoms; or an unsubstituted or substituted aryl radical or a C$_1$–C$_4$-alkylaryl radical, where aryl has the meaning of phenyl or naphthyl, and said substituents are halogen, C$_1$–C$_4$-alkyl, C$_1$–C$_4$-alkoxy, nitro or cyano; Z has the meaning of N or P, and $Y^-$ is an inorganic anion; and in formula (4) $R^{20}$ and $R^{21}$ are identical or different and are a linear or branched alkyl radical having 1 to 16 carbon atoms; x is an integer from 2 to 6 and s is an integer from 1 to 60; or one of the radicals $R^{20}$ and $R^{21}$ is hydrogen and the other one of the radicals is a linear or branched alkyl radical having 1 to 16 carbon atoms, x is an integer from 2 to 6 and s is an integer from 2 to 50, or the radicals $R^{20}$ and $R^{21}$ are hydrogen, x is an integer from 2 to 6 and s is an integer from 3 to 5.

2. A mixture of substances as claimed in claim 1, which comprise at least one compound of the formula (1) and at least one compound selected from the group of quaternary ammonium compounds of the formula (2), quaternary ammonium salts and phosphonium salts of the formula (3), polyethers of the formula (4) and crown ethers, in which in formula (2) $R^{11}$, $R^{12}$ and $R^{13}$ are identical or different and are a linear or branched radical of the formula —$(C_pH_{2p}O)_rR^{15}$ in which $R^{15}$ is hydrogen or a linear or branched alkyl radical having 1 to 8 carbon atoms, p is an integer from 1 to 5 and r is an integer from 2 to 10; or a linear or branched alkyl radical having 1 to 18 carbon atoms; or an unsubstituted phenyl or naphthyl radical; $R^{14}$ is a linear or branched radical of the formula —$(C_pH_{2p}O)_rR^{15}$, in which $R^{15}$ is hydrogen or a linear or branched alkyl radical having 1 to 8 carbon atoms, p is an integer from 1 to 5 and r is an integer from 2 to 10; and $X^-$ is fluoride, chloride, bromide, $\frac{1}{2}SO_4^{2-}$ or hydrogen sulfate.

3. A mixture of substances as claimed in claim 1, which comprises at least one compound of the formula (1) and at least one compound from the group of quaternary ammonium compounds of the formula (2).

* * * * *